US00PP34626P3

(12) United States Plant Patent
Olesen et al.

(10) Patent No.: US PP34,626 P3
(45) Date of Patent: Oct. 4, 2022

(54) ***CLEMATIS* PLANT NAMED 'EVIPO103'**

(50) Latin Name: *Clematis viticella*
Varietal Denomination: Evipo103

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,628

(22) Filed: Sep. 7, 2021

(65) Prior Publication Data

US 2022/0095514 P1 Mar. 24, 2022

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.poulsenroser.dk/en/clematis/ShowProduct/78160; Oct. 22, 2021; 1 page.*
http://www.newplantsandflowers.com/three-clematis-introductions-at-chelsea-2018/; May 3, 2018; 2 pages.*

* cited by examiner

*Primary Examiner* — Kent L Bell

(57) ABSTRACT

A new *Clematis* plant with a compact growth habit, profuse, red purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo103'.

This application claims priority to Plant Breeder's Rights Application Number 2020/2276, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2006 and the resulting seeds were planted the following winter in a controlled environment in Guernsey, Channel Islands, United Kingdom. The new variety named 'Evipo103' originated as a single seedling from the stated cross.

The new *Clematis* plant may be distinguished from its female seed parent and male pollen parent by the following characteristics. The female seed parent has mauve tepals while the new variety has red purple tepals. The male seed parent grows to a height of 80 cm in one season, while the new variety grows to a height of 50 to 60 cm.

The objective of the hybridization of this *Clematis* plant was to create a new and distinct variety for nursery culture with unique qualities such as:

1. Uniform and abundant red purple flowers;
2. Vigorous and very compact, mounding growth habit, making the variety suitable for container culture; and
3. Improved disease resistance.

This combination of qualities was lacking in *Clematis* plants that were in commercial cultivation and the qualities have been substantially achieved in the new variety.

'Evipo103' was selected by Mogens N. Olesen and Raymond J. Evison in their *Clematis* development program in the Channel Islands, United Kingdom in 2007. Asexual reproduction of 'Evipo103' by means of vegetative cuttings and traditional layering was first performed by Mogens N. Olesen and Raymond J. Evison in the nursery during the summer of 2007. This initial and subsequent asexual propagations have demonstrated that the characteristics of 'Evipo103' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo103'.

Specifically illustrated in FIG. 1 of the drawings are open flowers viewed from above and underneath, and tepals detached revealing reproductive flower parts.

Figure 1:
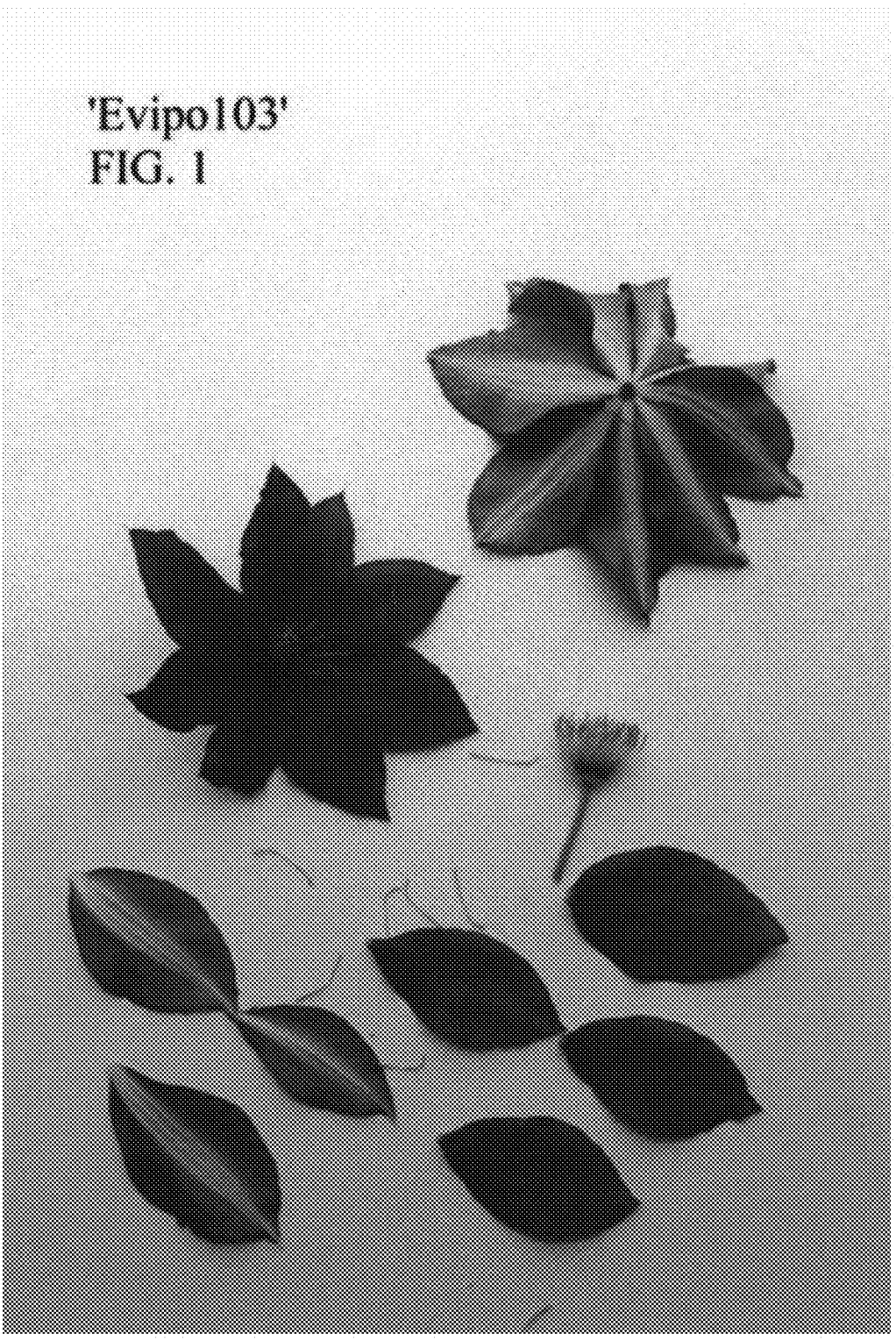
Figure 2:
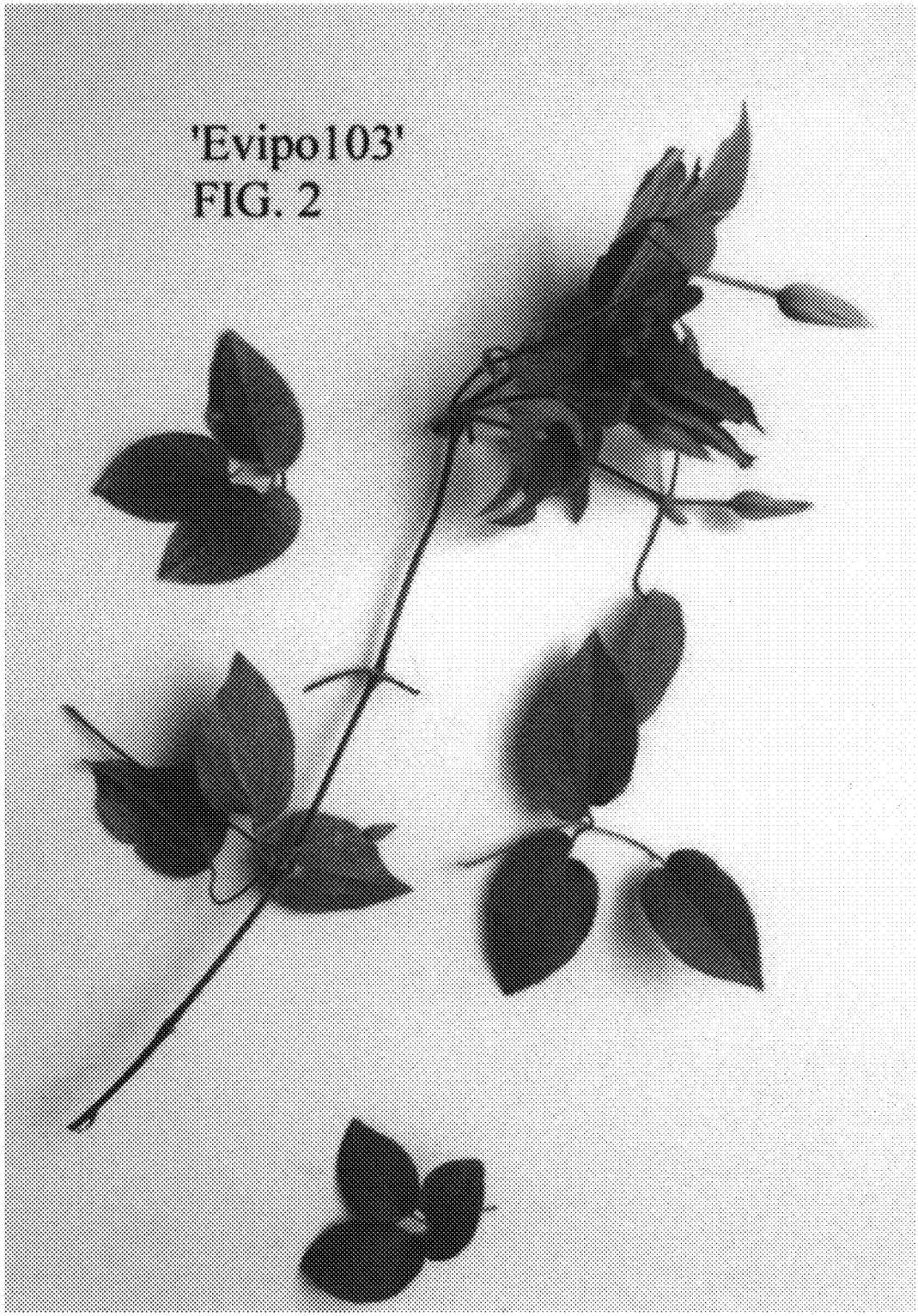
FIG. 2 shows a flowering branch, bare stem, and leaves detached.

Illustrated plants are 2 years of age.

DETAILED DESCRIPTION OF THE VARIETY

The following is a detailed description of 'Evipo103', as observed in its growth outdoors throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo070' described and illustrated in U.S. Plant Pat. No. 27,254 are compared to 'Evipo103' in Chart 1.

CHART 1

| | 'Evipo103' | 'Evipo070' |
|---|---|---|
| Flower diameter | 110 mm | 130 mm |
| Tepal upper surface upon opening | Red-Purple Group 60B with intonations of Red-Purple Group 61C | Red-Purple Group 61A |
| Tepal count | 8 | 6 |

Flower and flower bud:

*Blooming habit.*—Continuous. The natural flowering period is generally from April to September.

*Flower bud.*—Size: Normally 30 mm in length. Bud diameter is 11 mm. Bud form: Long campanulate, broad based. Bud color: Yellow-Green Group 144B. Texture: Pubescent.

*Pedicel.*—Surface Texture: Smooth, lightly pubescent. Length: On average 25 to 30 mm in length with 2 mm diameter. Color: Yellow-Green Group 144A. Strength: Moderately strong.

*Receptacle.*—Surface Texture: Lightly pubescent. Shape: Broad funnel. Size: 2 mm (h)×5 mm (w). Color: Yellow-Green Group 144A.

*Flower arrangement.*—Location on vine: New growth only. Borne: Singly and clusters of 3 to 9 flowers per flowering branch.

*Flower bloom.*—Size: On average, flowers are 110 mm in diameter and 15 mm in depth. Profile: Open flowers are nearly flat. Fragrance: None. Lasting Quality: Flowers normally remain up to 14 days on the plant.

*Tepals.*—Tepal Color: Upon opening, the upper surface of tepals are Red-Purple Group 60B with intonations of Red-Purple Group 61C. The tip of the apex is White N155B. The lower surface is Purple Group 76A and Purple Group N77B towards the margins. There is a central bar of Greyed-Green Group 193B. Quantity: Normally 8 tepals. Size: 65 to 70 mm in length by 38 mm wide. Shape: Individual tepal shape is elliptic. The tepal apex is mucronate. The tepal base acute. Apex Recurvature: None. Tepal Cross section: Flat. Margins: Entire. Moderately undulated. Persistence: Tepals drop off cleanly.

*Reproductive organs.*—Pollen: None observed. Anthers: Size: About 8 mm in length. Color: Greyed-Yellow Group 160D. Quantity: On average 35. Filaments: Color: White N155C with colorations of Violet Group 86C at base. Length: 10 mm. Pistils: Quantity: On average, 20. Stigmas: Inferior in location relative to the length of the filaments and the height of the anthers. Styles: Color: Yellow-White Group 158B. Length: 10 mm.

*Seed head characteristics.*—Seed not observed to date.

Plant:

*Plant form.*—Mounding.

*Plant growth.*—Very compact.

*Size.*—Seasons growth attains 50 to 60 cm in height. Average spread is 40 to 50 cm.

*Stems.*—Color: Juvenile stems are Yellow-Green Group 144A. Mature stems are Greyed-Orange Group 166B. Internodes: On average, 70 to 85 mm between nodes. Length: Normally 20 cm from the base of the plant to the flowering portion of the stem. Diameter: About 3 mm. Texture: Mature stems are ribbed.

*Plant foliage.*—Leaf characteristics: Deciduous. Arrangement: Trifoliate. Leaf Size: Compound leaves are about 120 mm (l)×130 mm (w). Leaflets are about 60 mm (l)×36 mm (w). Abundance: On average leaves per 10 cm of stem. Leaf Color: Juvenile upper Yellow-Green Group N144A. Juvenile lower Yellow-Green Group 144A. Mature upper Yellow-Green Group 144A. Mature lower Yellow-Green Group 144B. Stipules: Absent. Petioles: Size: Normally 50 mm in length by 2 mm diameter. Texture: Smooth. Color: Yellow-Green Group 144A with intonations of Greyed-Purple Group 183A. Petioloule: Size: About 30 mm in length by 2 mm diameter. Texture: Smooth. Color: Yellow-Green Group 144A with Greyed-Purple Group 183A. Leaflet Shape: Cordate. The base is rounded or oblique, and the apex is acute. Margin: Entire. Surface: The upper side is smooth, the lower side is smooth. Thickness: Moderate. Glossiness: Moderately glossy.

*Disease resistance.*—Subject to any disease that normally attacks the species. However the variety is more tolerant to *Clematis* wilt, *Ascochyta clematidina*, than some *Clematis* known to the inventors.

*Cold hardiness.*—The variety is tolerant to USDA Hardiness Zone 6.

*Heat tolerance.*—The variety has been found to be suitable for climate conditions found in the American Horticulture Society heat zone 7.

We claim:

1. A new and distinct variety of *Clematis* plant named 'Evipo103', substantially as described and illustrated, due to its abundant red purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo103'

'Evipo103'